US008722091B2

(12) United States Patent
Brynjelsen et al.

(10) Patent No.: US 8,722,091 B2
(45) Date of Patent: *May 13, 2014

(54) PREPARATION OF SUBMICRON SIZED NANOPARTICLES VIA DISPERSION LYOPHILIZATION

(75) Inventors: Sean Brynjelsen, Lake in the Hills, IL (US); Mark Doty, Grayslake, IL (US); James E. Kipp, Wauconda, IL (US); Nailesh Jayswal, Bensonville, IL (US); Krishnaswamy Narayanan, Waukesha, WI (US)

(73) Assignee: Baxter International Inc., Deerfield, IL (US)

(*) Notice: Subject to any disclaimer, the term of this patent is extended or adjusted under 35 U.S.C. 154(b) by 684 days.

This patent is subject to a terminal disclaimer.

(21) Appl. No.: 10/920,578

(22) Filed: Aug. 17, 2004

(65) Prior Publication Data
US 2005/0013868 A1    Jan. 20, 2005

Related U.S. Application Data

(63) Continuation of application No. 10/183,035, filed on Jun. 26, 2002, now Pat. No. 6,835,396, which is a continuation-in-part of application No. 09/964,273, filed on Sep. 26, 2001.

(51) Int. Cl.
*A61K 9/14* (2006.01)
(52) U.S. Cl.
CPC ........................................ *A61K 9/14* (2013.01)
USPC ........................................................ 424/489
(58) Field of Classification Search
CPC ...................................................... A61K 9/14
See application file for complete search history.

(56) References Cited

U.S. PATENT DOCUMENTS

| | | | |
|---|---|---|---|
| 2,525,071 A | 10/1950 | Hardy et al. |
| 2,720,203 A | 10/1955 | Burns et al. |
| 2,745,785 A | 5/1956 | Bruce et al. |
| 3,685,261 A | 8/1972 | McIlvaine et al. |
| 4,056,635 A | 11/1977 | Glen et al. |
| 4,073,943 A | 2/1978 | Wretlind et al. |
| 4,340,589 A | 7/1982 | Uemura et al. |
| 4,452,817 A | 6/1984 | Glen et al. |
| 4,540,602 A | 9/1985 | Motoyama et al. |
| 4,606,670 A | 8/1986 | Frank et al. |
| 4,606,940 A | 8/1986 | Frank et al. |
| 4,608,278 A | 8/1986 | Frank et al. |
| 4,622,219 A | 11/1986 | Haynes |
| 4,725,442 A | 2/1988 | Haynes |
| 4,786,735 A | 11/1988 | Graboyes et al. |
| 4,798,846 A | 1/1989 | Glen et al. |
| 4,826,689 A | 5/1989 | Violanto |
| 4,857,552 A | 8/1989 | Rosenberg et al. |
| 4,973,465 A | 11/1990 | Baurain et al. |
| 4,997,454 A | 3/1991 | Violante et al. |
| 5,017,609 A | 5/1991 | Escobar et al. |
| 5,023,271 A | 6/1991 | Vigne et al. |
| 5,049,322 A | 9/1991 | Devissaguet et al. |
| 5,078,994 A | 1/1992 | Nair et al. |
| 5,091,187 A | 2/1992 | Haynes |
| 5,091,188 A | 2/1992 | Haynes |
| 5,100,591 A | 3/1992 | Leclef et al. |
| 5,118,528 A | 6/1992 | Fessi et al. |
| 5,122,543 A | 6/1992 | Khanna |
| 5,133,908 A | 7/1992 | Stainmesse et al. |
| 5,145,684 A | 9/1992 | Liversidge et al. |
| 5,151,264 A | 9/1992 | Samain et al. |
| 5,152,923 A | 10/1992 | Weder et al. |
| 5,171,566 A | 12/1992 | Mizushima et al. |
| 5,174,930 A | 12/1992 | Stainmesse et al. |
| 5,188,837 A | 2/1993 | Domb |
| 5,246,707 A | 9/1993 | Haynes |
| 5,250,236 A | 10/1993 | Gasco |
| 5,269,979 A | 12/1993 | Fountain |
| 5,298,262 A | 3/1994 | Na et al. |
| 5,302,401 A * | 4/1994 | Liversidge et al. ........... 424/501 |
| 5,306,519 A | 4/1994 | Peterson et al. |
| 5,314,506 A | 5/1994 | Midler, Jr. et al. |
| 5,318,767 A | 6/1994 | Liversidge |
| 5,326,552 A | 7/1994 | Na et al. |
| 5,336,507 A | 8/1994 | Na et al. |
| 5,340,564 A | 8/1994 | Illig et al. |

(Continued)

FOREIGN PATENT DOCUMENTS

| | | |
|---|---|---|
| EP | 0275 796 B2 | 7/1988 |
| EP | 0379 379 B1 | 1/1990 |

(Continued)

OTHER PUBLICATIONS

Davis et al., "Pulmonary Perfusion Imaging: Acute Toxicity and Safety Factors as Function of Particle Size", J.Nucl Med., vol. 19 (1978), pp. 1209-1213.
Schroeder et al., "Physiological Effects of Subvisible Microspheres Administered Intravenously to Beagle Dogs", Journal of Pharmaceutical Sciences, vol. 67, No. 4, Apr. 1978, pp. 508-512.
Yokel et al., "Acute Toxcoty of Latex Microspheres", Toxicity Letters, vol. 9 (1981), pp. 165-170.
Allen et al., "Critical Evaluation of Acute Cardiopulminary Toxcity of Microspheres", J. Nucl Med., vol. 19 (1987), pp. 1204-1208.
B. Sjostrom et al., "Preparation of Submicron Drug Particles in Lecithin-Stabilized O/W Emulsions I. Model Studies of the Precipitation of Cholesteryl Acetate", Int. J. Pharm, 88 (1992) pp. 53-62.

(Continued)

*Primary Examiner* — Susan Tran
(74) *Attorney, Agent, or Firm* — Marshall, Gerstein & Borun LLP

(57) ABSTRACT

The present invention relates to a process for preparing submicron sized nanoparticles of a poorly water soluble compound by lyophilizing a dispersion or microdispersion of a multiphase system having an organic phase and an aqueous phase, the organic phase having the poorly water soluble organic compound therein. The method is preferably used to prepare nanoparticles of a poorly water soluble, pharmaceutically active compound suitable for in vivo delivery, particularly by parenteral routes.

47 Claims, 2 Drawing Sheets

(56) References Cited

U.S. PATENT DOCUMENTS

| | | | |
|---|---|---|---|
| 5,346,702 A | 9/1994 | Na et al. | |
| 5,352,459 A | 10/1994 | Hollister et al. | |
| 5,354,563 A | 10/1994 | Toyotama | |
| 5,389,263 A | 2/1995 | Gallagher et al. | |
| 5,399,363 A | 3/1995 | Liversidge et al. | |
| 5,417,956 A | 5/1995 | Moser | |
| 5,429,824 A | 7/1995 | June | |
| 5,447,710 A | 9/1995 | Na et al. | |
| 5,466,646 A | 11/1995 | Moser | |
| 5,470,583 A | 11/1995 | Na et al. | |
| 5,474,989 A | 12/1995 | Hashimoto et al. | |
| 5,494,683 A | 2/1996 | Liversidge et al. | |
| 5,510,118 A | 4/1996 | Bosch et al. | |
| 5,518,187 A | 5/1996 | Bruno et al. | |
| 5,518,738 A | 5/1996 | Eickhoff et al. | |
| 5,534,270 A | 7/1996 | De Castro | |
| 5,543,133 A | 8/1996 | Swanson et al. | |
| RE35,338 E | 9/1996 | Haynes | |
| 5,552,160 A | 9/1996 | Liversidge et al. | |
| 5,560,932 A | 10/1996 | Bagchi et al. | |
| 5,560,933 A | 10/1996 | Soon-Shiong et al. | |
| 5,565,383 A | 10/1996 | Sakai | |
| 5,569,448 A | 10/1996 | Wong et al. | |
| 5,573,783 A | 11/1996 | Desieno et al. | |
| 5,578,325 A | 11/1996 | Domb et al. | |
| 5,580,579 A | 12/1996 | Ruddy et al. | |
| 5,587,143 A | 12/1996 | Wong | |
| 5,591,456 A | 1/1997 | Franson et al. | |
| 5,605,785 A | 2/1997 | Texter et al. | |
| 5,626,864 A | 5/1997 | Rosenberg et al. | |
| 5,635,609 A | 6/1997 | Levy et al. | |
| 5,637,568 A | 6/1997 | Orsolini et al. | |
| 5,637,625 A | 6/1997 | Haynes | |
| 5,641,515 A | 6/1997 | Ramtoola | |
| 5,641,745 A | 6/1997 | Ramtoola | |
| 5,660,858 A | 8/1997 | Parikh et al. | |
| 5,662,883 A | 9/1997 | Bagchi et al. | |
| 5,662,932 A | 9/1997 | Amselem et al. | |
| 5,665,331 A | 9/1997 | Bagchi et al. | |
| 5,665,383 A | 9/1997 | Grinstaff et al. | |
| 5,679,576 A | 10/1997 | Kawai et al. | |
| 5,707,634 A | 1/1998 | Schmitt | |
| 5,716,642 A | 2/1998 | Bagchi et al. | |
| 5,720,551 A | 2/1998 | Shechter | |
| 5,766,635 A | 6/1998 | Spenleuhauer et al. | |
| 5,780,062 A | 7/1998 | Frank et al. | |
| 5,833,891 A | 11/1998 | Subramaniam et al. | |
| 5,858,410 A | 1/1999 | Muller et al. | |
| 5,862,999 A | 1/1999 | Czekai et al. | |
| 5,874,111 A | 2/1999 | Maitra et al. | |
| 5,874,574 A | 2/1999 | Johnston et al. | |
| 5,885,486 A | 3/1999 | Westesen et al. | |
| 5,885,491 A * | 3/1999 | Galan Valdivia et al. | 264/4.1 |
| 5,885,984 A | 3/1999 | MacLeod et al. | |
| 5,886,239 A | 3/1999 | Kudzma et al. | |
| 5,916,583 A | 6/1999 | Broberg et al. | |
| 5,916,596 A * | 6/1999 | Desai et al. | 424/489 |
| 5,922,355 A | 7/1999 | Parikh et al. | |
| 5,939,100 A | 8/1999 | Albrechtsen et al. | |
| 5,981,719 A | 11/1999 | Woiszwillo et al. | |
| 5,989,583 A | 11/1999 | Amselem | |
| 6,007,845 A | 12/1999 | Domb et al. | |
| 6,039,981 A | 3/2000 | Woo et al. | |
| 6,045,826 A | 4/2000 | Borowy-Borowski et al. | |
| 6,045,829 A | 4/2000 | Liversidge et al. | |
| 6,048,550 A | 4/2000 | Chan et al. | |
| 6,063,138 A | 5/2000 | Hanna et al. | |
| 6,063,910 A | 5/2000 | Debenedetti et al. | |
| 6,068,858 A | 5/2000 | Liversidge et al. | |
| 6,083,514 A | 7/2000 | Chang et al. | |
| 6,086,376 A | 7/2000 | Moussa et al. | |
| 6,090,925 A | 7/2000 | Woiszwillo et al. | |
| 6,090,983 A | 7/2000 | Yokoyama et al. | |
| 6,100,302 A | 8/2000 | Pejaver et al. | |
| 6,132,750 A | 10/2000 | Perrier et al. | |
| 6,139,870 A | 10/2000 | Verrecchia | |
| 6,143,211 A | 11/2000 | Mathiowitz et al. | |
| 6,143,778 A | 11/2000 | Gautier et al. | |
| 6,146,663 A | 11/2000 | Bissery et al. | |
| 6,153,219 A | 11/2000 | Creeth et al. | |
| 6,153,225 A | 11/2000 | Lee et al. | |
| 6,165,506 A | 12/2000 | Jain et al. | |
| 6,177,103 B1 | 1/2001 | Pace et al. | |
| 6,197,757 B1 | 3/2001 | Perrier et al. | |
| 6,207,134 B1 | 3/2001 | Fahlvik et al. | |
| 6,207,178 B1 | 3/2001 | Westesen et al. | |
| 6,214,384 B1 | 4/2001 | Pallado et al. | |
| 6,217,886 B1 | 4/2001 | Onyuksel et al. | |
| 6,221,332 B1 | 4/2001 | Thumm et al. | |
| 6,221,398 B1 | 4/2001 | Jakupovic et al. | |
| 6,221,400 B1 | 4/2001 | Liversidge et al. | |
| 6,228,399 B1 | 5/2001 | Parikh et al. | |
| 6,231,890 B1 | 5/2001 | Naito et al. | |
| 6,235,224 B1 | 5/2001 | Mathiowitz | |
| 6,238,677 B1 | 5/2001 | Fanta et al. | |
| 6,238,694 B1 | 5/2001 | Gasco | |
| 6,245,349 B1 | 6/2001 | Yiv et al. | |
| 6,248,363 B1 | 6/2001 | Patel et al. | |
| 6,261,537 B1 | 7/2001 | Klaveness et al. | |
| 6,264,922 B1 | 7/2001 | Wood et al. | |
| 6,267,989 B1 | 7/2001 | Liversidge | |
| 6,268,053 B1 | 7/2001 | Woiszwillo et al. | |
| 6,270,806 B1 | 8/2001 | Liversidge et al. | |
| 6,294,204 B1 | 9/2001 | Rossling et al. | |
| 6,299,906 B1 | 10/2001 | Bausch et al. | |
| 6,306,406 B1 | 10/2001 | Deluca | |
| 6,310,094 B1 | 10/2001 | Liu et al. | |
| 6,337,092 B1 | 1/2002 | Khan et al. | |
| 6,344,271 B1 | 2/2002 | Yadav et al. | |
| 6,346,533 B1 | 2/2002 | Cha et al. | |
| 6,365,191 B1 | 4/2002 | Burman et al. | |
| 6,375,986 B1 | 4/2002 | Ryde et al. | |
| 6,387,409 B1 | 5/2002 | Khan et al. | |
| 6,391,832 B2 | 5/2002 | Lyons et al. | |
| 6,395,300 B1 | 5/2002 | Straub et al. | |
| 6,428,814 B1 | 8/2002 | Bosch et al. | |
| 6,458,387 B1 | 10/2002 | Scott et al. | |
| 6,461,642 B1 | 10/2002 | Bisrat et al. | |
| 6,462,093 B1 | 10/2002 | Miyamoto et al. | |
| 6,476,003 B1 * | 11/2002 | Jordan et al. | 514/54 |
| 6,482,518 B1 | 11/2002 | Short et al. | |
| 6,528,540 B2 | 3/2003 | Liu et al. | |
| 6,607,784 B2 * | 8/2003 | Kipp et al. | 427/213.3 |
| 6,616,869 B2 | 9/2003 | Mathiowitz et al. | |
| 6,682,761 B2 * | 1/2004 | Pace et al. | 424/489 |
| 6,723,347 B1 * | 4/2004 | Yamagata et al. | 424/489 |
| 6,835,396 B2 * | 12/2004 | Brynjelsen et al. | 424/489 |
| 6,869,617 B2 | 3/2005 | Kipp et al. | |
| 6,884,436 B2 * | 4/2005 | Kipp et al. | 424/489 |
| 7,112,340 B2 * | 9/2006 | Kipp et al. | 424/489 |
| 2001/0007678 A1 | 7/2001 | Baert et al. | |
| 2001/0025058 A1 | 9/2001 | Borowy-Borowski et al. | |
| 2001/0042932 A1 | 11/2001 | Mathiowitz et al. | |
| 2002/0012675 A1 | 1/2002 | Jain et al. | |
| 2002/0012704 A1 | 1/2002 | Pace et al. | |
| 2002/0036776 A1 | 3/2002 | Shimaoka | |
| 2002/0041896 A1 | 4/2002 | Straub et al. | |
| 2002/0048610 A1 | 4/2002 | Cima et al. | |
| 2002/0054912 A1 | 5/2002 | Kim et al. | |
| 2002/0076347 A1 | 6/2002 | Maerz | |
| 2002/0110599 A1 | 8/2002 | Auweter et al. | |
| 2002/0127278 A1 | 9/2002 | Kipp et al. | |
| 2002/0168402 A1 | 11/2002 | Kipp et al. | |
| 2002/0182107 A1 | 12/2002 | Laugharn et al. | |
| 2003/0003155 A1 | 1/2003 | Kipp et al. | |
| 2003/0031719 A1 | 2/2003 | Kipp et al. | |
| 2003/0044433 A1 | 3/2003 | Werling et al. | |
| 2003/0054042 A1 | 3/2003 | Liversidge et al. | |
| 2003/0059472 A1 | 3/2003 | Brynjelsen et al. | |
| 2003/0072807 A1 * | 4/2003 | Wong et al. | 424/490 |
| 2003/0077329 A1 | 4/2003 | Kipp et al. | |
| 2003/0096013 A1 * | 5/2003 | Werling et al. | 424/489 |
| 2003/0100568 A1 | 5/2003 | Werling et al. | |
| 2003/0170279 A1 | 9/2003 | Lambert et al. | |

(56) References Cited

U.S. PATENT DOCUMENTS

| | | |
|---|---|---|
| 2003/0206959 A9 | 11/2003 | Kipp et al. |
| 2003/0211083 A1 | 11/2003 | Vogel et al. |
| 2004/0022861 A1 | 2/2004 | Williams |
| 2004/0022862 A1 | 2/2004 | Kipp et al. |
| 2004/0043077 A1 | 3/2004 | Brown |
| 2004/0245662 A1 | 12/2004 | Chaubal et al. |
| 2004/0256749 A1 | 12/2004 | Chaubal |
| 2005/0013868 A1 | 1/2005 | Brynjelsen et al. |
| 2005/0037083 A1 | 2/2005 | Brynjelsen et al. |
| 2005/0244503 A1 | 11/2005 | Rabinow et al. |

FOREIGN PATENT DOCUMENTS

| | | | |
|---|---|---|---|
| EP | 0423697 A2 | 4/1991 | |
| EP | 0498 482 B1 | 8/1992 | |
| EP | 0499 299 B1 | 8/1992 | |
| EP | 0517 565 B1 | 12/1992 | |
| EP | 0349 428 B1 | 1/1993 | |
| EP | 0377 477 B1 | 3/1993 | |
| EP | 0535 534 A1 | 4/1993 | |
| EP | 0169 618 B2 | 11/1993 | |
| EP | 0577 215 A1 | 5/1994 | |
| EP | 0600 532 A2 | 6/1994 | |
| EP | 0601 618 A2 | 6/1994 | |
| EP | 0601 619 A2 | 6/1994 | |
| EP | 0602 700 A2 | 6/1994 | |
| EP | 0602 702 A1 | 6/1994 | |
| EP | 0600532 A2 | 6/1994 | |
| EP | 0605 024 A2 | 7/1994 | |
| EP | 0207 134 B1 | 8/1994 | |
| EP | 0602 700 A3 | 12/1994 | |
| EP | 0600 532 A3 | 2/1995 | |
| EP | 0642992 A2 | 3/1995 | |
| EP | 0605 024 A3 | 4/1995 | |
| EP | 0652011 A1 | 5/1995 | |
| EP | 0601 618 A3 | 11/1995 | |
| EP | 0601 619 A3 | 11/1995 | |
| EP | 0820 300 B1 | 4/1996 | |
| EP | 0372 070 B1 | 1/1997 | |
| EP | 0754 034 B1 | 1/1997 | |
| EP | 0644 755 B1 | 3/1997 | |
| EP | 0832 569 A2 | 4/1998 | |
| EP | 0730 406 B1 | 7/1998 | |
| EP | 0857484 A1 | 8/1998 | |
| EP | 0988 863 B1 | 3/2000 | |
| EP | 0831 770 B1 | 8/2000 | |
| EP | 1023 050 A1 | 8/2000 | |
| EP | 0808 154 B1 | 12/2000 | |
| EP | 0720 471 B1 | 4/2001 | |
| EP | 0804 162 B1 | 9/2001 | |
| EP | 0828 479 B1 | 10/2001 | |
| EP | 0788 350 B1 | 2/2002 | |
| EP | 0752 245 B1 | 5/2002 | |
| EP | 1210 942 A2 | 6/2002 | |
| EP | 1012 204 B1 | 1/2003 | |
| EP | 1156 788 B1 | 1/2003 | |
| EP | 1105 109 B1 | 4/2003 | |
| EP | 0812 187 B1 | 5/2003 | |
| EP | 0832 569 B1 | 11/2003 | |
| EP | 0988 863 A2 | 4/2004 | |
| FR | 2817478 A1 | 6/2002 | |
| FR | 2838969 A1 | 10/2003 | |
| JP | 023069202 | 12/1990 | |
| JP | H2-306902 | 12/1990 | |
| WO | WO 85/00011 A1 | 1/1985 | |
| WO | WO 86/03676 A1 | 7/1986 | |
| WO | WO 89/11850 A1 | 12/1989 | |
| WO | WO 90/03782 A2 | 4/1990 | |
| WO | WO 90/15593 A1 | 12/1990 | |
| WO | WO 91/06292 A1 | 5/1991 | |
| WO | WO-91/07170 A1 | 5/1991 | |
| WO | WO 91/12794 A1 | 9/1991 | |
| WO | WO 91/16068 A1 | 10/1991 | |
| WO | WO 92/00731 A1 | 1/1992 | |
| WO | WO 92/03380 A1 | 3/1992 | |
| WO | WO-92/08447 A1 | 5/1992 | |
| WO | WO 92/17214 A2 | 10/1992 | |
| WO | WO 93/25190 A1 | 12/1993 | |
| WO | WO 94/07999 A1 | 4/1994 | |
| WO | WO 94/20072 A1 | 9/1994 | |
| WO | WO 95/05164 A1 | 2/1995 | |
| WO | WO 95/27482 A1 | 10/1995 | |
| WO | WO 95/33488 A1 | 12/1995 | |
| WO | WO 96/00567 A1 | 1/1996 | |
| WO | WO 96/14833 A1 | 5/1996 | |
| WO | WO 96/20698 A2 | 7/1996 | |
| WO | WO 96/24336 A1 | 8/1996 | |
| WO | WO 96/24340 A1 | 8/1996 | |
| WO | WO 96/25150 A1 | 8/1996 | |
| WO | WO 96/25152 A1 | 8/1996 | |
| WO | WO 96/25918 A1 | 8/1996 | |
| WO | WO 96/31231 A1 | 10/1996 | |
| WO | WO 97/03651 A1 | 2/1997 | |
| WO | WO 97/03657 A1 | 2/1997 | |
| WO | WO 97/14407 A1 | 4/1997 | |
| WO | WO 97/30695 A1 | 8/1997 | |
| WO | WO 97/36611 A1 | 10/1997 | |
| WO | WO 97/41837 A2 | 11/1997 | |
| WO | WO 97/44014 A1 | 11/1997 | |
| WO | WO 98/01162 A2 | 1/1998 | |
| WO | WO 98/07410 A1 | 2/1998 | |
| WO | WO 98/07414 A1 | 2/1998 | |
| WO | WO 98/14170 A1 | 4/1998 | |
| WO | WO 98/14174 A1 | 4/1998 | |
| WO | WO 98/14180 A1 | 4/1998 | |
| WO | WO 98/24450 A1 | 6/1998 | |
| WO | WO-98/31346 A1 | 7/1998 | |
| WO | WO 98/35666 A1 | 8/1998 | |
| WO | WO-98/56362 A1 | 12/1998 | |
| WO | WO 98/57967 A1 | 12/1998 | |
| WO | WO 99/00113 A1 | 1/1999 | |
| WO | WO 99/02665 A1 | 1/1999 | |
| WO | WO 99/03450 A1 | 1/1999 | |
| WO | WO-99/06022 A1 | 2/1999 | |
| WO | WO 99/16443 A1 | 4/1999 | |
| WO | WO 99/29316 A1 | 6/1999 | |
| WO | WO 99/30833 A1 | 6/1999 | |
| WO | WO 99/32156 A2 | 7/1999 | |
| WO | WO 99/33467 A1 | 7/1999 | |
| WO | WO 99/38493 A1 | 8/1999 | |
| WO | WO 99/39700 A1 | 8/1999 | |
| WO | WO 9939700 A1 * | 8/1999 | |
| WO | WO 99/49846 A2 | 10/1999 | |
| WO | WO 99/49848 A2 | 10/1999 | |
| WO | WO-99/53901 A1 | 10/1999 | |
| WO | WO 99/59550 A1 | 11/1999 | |
| WO | WO 99/61001 A1 | 12/1999 | |
| WO | WO 99/65469 A3 | 12/1999 | |
| WO | WO 00/06152 A1 | 2/2000 | |
| WO | WO 00/09096 A1 | 2/2000 | |
| WO | WO 00/12124 A1 | 3/2000 | |
| WO | WO 00/12125 A1 | 3/2000 | |
| WO | WO 00/18374 A1 | 4/2000 | |
| WO | WO 00/27363 A1 | 5/2000 | |
| WO | WO 00/30615 A1 | 6/2000 | |
| WO | WO 00/30616 A1 | 6/2000 | |
| WO | WO 00/37050 A1 | 6/2000 | |
| WO | WO 00/40220 A1 | 7/2000 | |
| WO | WO 00/51572 B1 | 9/2000 | |
| WO | WO-00/59471 A1 | 10/2000 | |
| WO | WO-00/61108 A1 | 10/2000 | |
| WO | WO 00/71079 A2 | 11/2000 | |
| WO | WO-00/72820 A2 | 12/2000 | |
| WO | WO 01/12155 A1 | 2/2001 | |
| WO | WO 01/17546 A1 | 3/2001 | |
| WO | WO 01/21154 A2 | 3/2001 | |
| WO | WO 01/26635 A2 | 4/2001 | |
| WO | WO 01/62374 A2 | 8/2001 | |
| WO | WO 01/64164 A2 | 9/2001 | |
| WO | WO 01/21154 A3 | 10/2001 | |
| WO | WO 01/80828 A2 | 11/2001 | |
| WO | WO 01/85345 A1 | 11/2001 | |
| WO | WO 01/87264 A2 | 11/2001 | |

(56) References Cited

FOREIGN PATENT DOCUMENTS

| WO | WO 02/17883 A2 | 3/2002 |
|---|---|---|
| WO | WO-02/22195 A2 | 3/2002 |
| WO | WO 02/24163 A1 | 3/2002 |
| WO | WO 02/24169 A1 | 3/2002 |
| WO | WO-02/26324 A2 | 4/2002 |
| WO | WO 02/43702 A2 | 6/2002 |
| WO | WO 02/51386 A2 | 7/2002 |
| WO | WO 02/55059 A2 | 7/2002 |
| WO | WO 02/60411 A2 | 8/2002 |
| WO | WO 02/72070 A1 | 9/2002 |
| WO | WO 02/72071 A1 | 9/2002 |
| WO | WO 02/74282 A1 | 9/2002 |
| WO | WO-02/76446 A1 | 10/2002 |
| WO | WO 02/80678 A1 | 10/2002 |
| WO | WO 02/80883 A2 | 10/2002 |
| WO | WO 02/82074 A1 | 10/2002 |
| WO | WO 02/089773 A2 | 11/2002 |
| WO | WO-03/024424 | 3/2003 |
| WO | WO 03/026611 A2 | 4/2003 |
| WO | WO 03/035031 A1 | 5/2003 |
| WO | WO 03/045330 A2 | 6/2003 |
| WO | WO 03/045660 A1 | 6/2003 |
| WO | WO 03/026611 A3 | 7/2003 |
| WO | WO 03/045330 A3 | 12/2003 |
| WO | WO-2004/032858 A2 | 4/2004 |
| WO | WO-2004/056666 A1 | 7/2004 |
| WO | WO-2004/093795 A2 | 11/2004 |
| WO | WO 2004/103348 A2 | 12/2004 |
| WO | WO-2004/112747 A2 | 12/2004 |
| WO | WO 2004/103348 A3 | 1/2005 |

OTHER PUBLICATIONS

B. Sjostrom et al., "A Method for the the Preparation of Submicron Particles of Sparingly Water-Soluble Drugs by Precipitation in Oil-In-Water Emulsions. II: Influence of the Emulsifier, The Solvent and the Drug Substance", J. Pharm. Sci., 82(6), (1992) pp. 584-589.

Duncker and Reichelt, "Effects of the Pharmaceutical Cosolvent Hydroxypropyl-beta-cyclodextrin on Porcine Corneal Endothelium", Graefe's Archive for Clinical and Experimental Ophthalmology (Germany). 236/5 (1998). pp. 380-389.

Volcheck and Dellen, "Anaphylaxis to Intravenous Cyclosporine and Tolerance to Oral Cyclosporine, Case Report and Review", Annals of Allergy, Asthma and Immunology, 80 (1998), pp. 159-163.

Singla et al., "Paclitaxel and its Formulations", International Journal of Pharmaceutics, 235/1-2 (2002). pp. 179-192.

B. Sjostrom, et al., "The Formation of Submicron Organic Particles by Precipitation in an Emulsion", J. Dispersion Science and Technology, 15(1), 89-117, (1994).

Avanti Polar Lipids, Inc., website printout, www.avantilipids.com, "Synthetic Products—Functionalized Phospholipids: Lipids for Conjugation of Proteins/Peptides/Drugs to Lipsomes" (7 pgs). Mar. 2003.

Avanti Polar Lipids, Inc., website printout, www.avantilipids.com, "Polymer and Polymerizable Lipids: Functionalized PEG Lipids" (3 pgs), Mar. 2003.

Avanti Polar Lipids, Inc., website printout, www.avantilipids.com, "Polymer and Polymerizable Lipids: Poly(ethylene glycol)-Lipid Conjugates" (8 pgs), Mar. 2003.

Graham, D.T., et al., "The Effects of Freezing on Commercial Insulin Suspensions", International Journal of Pharmaceutics, 1978.

Bender et al., "Efficiency of Nanoparticles as a Carrier for Antiviral Agents in Human Immunodeficiency Virus-Infected Human Monocytes/Macrophases In Vitro", Antimicrobial Agents and Chemotherapy, 40(6), pp. 1467-1471, Jun. 1996.

H. von Briesen, "Controled Release of Antiretroviral Drugs", AIDS Rev., 2, pp. 31-38, 2000.

Aquaro, et al., "Macrophages and HIV infection: therapeutical approaches toward this strateaic virus reservoir", Antiviral Research 55, pp. 209-225, 2002.

Crowe, et al., "The contribution of monocyte infection and trafficking to viral persistence, and maintenance of the viral reservoir in HIV infection", Journal of Leukocyte Biology, pp. 635-641, Nov. 2003.

Fischer-Smith et al., CNS invasion by CD14+/CD16+ peripheral blood-derived monocytes in HIV dementia: perivascular accumulation and reservoir of HIV infection, Journal of NeuroVirology, 7, pp. 528-541, 2001.

Igarashi et al., "Macrophage are the principal reservoir and sustain high virus loads in rhesus macaques after the depletion of CD4+ T cells by a highly pathogenic simian immunodeficiency virus/HIV type 1 chimera (SHIV): Implications for HIV-1 infections of humans", PNAS, 98(2), pp. 658-663, Jan. 16, 2001.

Limoges et al., poster presentation, 11th Conference on Retroviruses and Opportunistic Infections. Feb. 8-11, 2004.

Moghimi et al., "Long-Circulating and Target-Specific Nanoparticles: Theory to Practice", Pharmacological Reviews, 53, pp. 283-318, 2001.

Nesbit et al., "In Vitro and Animal Models of Human Immunodeficiency Virus Infection of the Central Nervous System", Clinical and Diagnostic Laboratory Immunology, 9(3), pp. 515-524, May 2002.

Nottet et al., "HIV-1 Entry into Brain: Mechanisms for the Infiltration of HIV-1 infected Macrophages Across the Blood-Brain Barrier", The Neurology of AIDS, p. 55, 1998.

Perno et al., "Relative Potency of Protease Inhibitors in Monocytes/Macrophages Acutely and Chronically Infected with Human Immunodeficiency Virus", The Journal of Infectious Diseases, 178, pp. 413-422, 1998.

Sawchuk et al., "Investigation of distribution, transport and uptake of an anti-HIV drugs to the central nervous system", Advanced Drug Delivery Reviews, 39, pp. 5-31, 1999.

Solas et al., "Discrepancies between Protease Inhibitor Concentrations and Viral Loan in Reservoirs and Sanctuary Sites in Human Immunodeficiency Virus-Infected Patients", Antimicrobiology Agents and Chemotherapy, 47 (1), pp. 238-243, Jan. 2003.

Shrayer, et al., "Ceramide, a mediator of apoptosis, synergizes with paclitaxel to induce regression of the L 3.6 human pancreatic carcinoma implanted in SCDI mice", Journal of Clinical Oncology, vol. 22, No. 14S, Abstract, 2004:2135.

Schroeder et al., "Distribution of Radiolabeled Subvisible Microspheres after Intravenous Administration to Beagle Dogs", Journal of Pharmaceutical Sciences, vol. 67, No. 4, pp. 504-507, Apr. 1978.

Allen et al., "Effects on the murine mononuclear phagocyte system of chronic administration of liposomes containing drug or lipid a compared with empty liposomes", Can. J. Physiol. Pharmacol., vol. 65, pp. 185-190, 1987.

Heiati et al., "Solid lipid nanoparticles as drug carriers: II. Plasma stability and biodistribution of solid lipid nanoparticles containing the lipophilic prodrug 3'-azido-3'-deoxythymidine palmitate in mice," Int. J. Pharmaceutics, 174:71-80 (1998).

Li et al., Poly(vinyl alcohol) nanoparticles prepared by freezing-thawing process for protein/peptide drug delivery, J. Control. Release, 56:117-26 (1998).

Lobenberg et al., "Body distribution of azidothymidine bound to hexyl-cyanoacrylate nanoparticles after i.v. injection to rats," J. Control. Release, 50:21-30 (1998).

Lobenberg et al., "Macrophage targeting of azidothymidine: a promising strategy for AIDS therapy," AIDS Res. Hum. Retroviruses, 12:1709-1715 (1996).

Mroczka, "Integral nsform technique in particle sizing," J. Aerosol Sci., 20:1075-1077 (1989).

Nonfinal office action from U.S. Appl. No. 11/425,122, dated May 26, 2010.

Nonfinal office action from U.S. Appl. No. 11/425,125, dated Jun. 7, 2010.

Rabinow, "Nanosuspensions in drug delivery," Nat. Rev. Drug Discov., 3:785-796 (2004).

Subramaniam et al., "Pharmaceutical processing with supercritical carbon dioxide," J. Pharm. Sci., 86:885-890 (1997).

(56) References Cited

OTHER PUBLICATIONS

Pikal et al., The impact of the freezing stage in lyophilization: effects of the ice nucleation temperature on process design and product quality, *American Pharmaceutical Review* (2008). Downloaded from the Internet at: <http://americanpharmaceutical review.com/View/Article.aspx?ContentID-148>.

USPTO Office Action issued in U.S. Appl. No. 11/425,122, dated Oct. 26, 2010.

Anonymous, Crystal growing. 9 pages. Retrieved from the Internet on Aug. 20, 2007: <URL: http://www.chem.tamu.edu/xray/pdf/guide%20to%20crystal%20growth.pdf>.

Ricketts, Project Habbakuk, Retrieved from the Internet on Aug. 20, 2007, <URL: http:www.mysteriesofcanada.com/Alberta/habbakuk.htm>.

US 5,849,884, 12/1998, Woiszwillo (withdrawn)

\* cited by examiner

US 8,722,091 B2

PREPARATION OF SUBMICRON SIZED NANOPARTICLES VIA DISPERSION LYOPHILIZATION

CROSS REFERENCE TO RELATED APPLICATIONS

This application is a continuation of U.S. patent application Ser. No. 10/183,035, filed on Jun. 26, 2002 now U.S. Pat. No. 6,835,396 which is a continuation-in-part of U.S. patent application Ser. No. 09/964,273,, filed Sep. 26, 2001.

FEDERALLY SPONSORED RESEARCH OR DEVELOPMENT

Not Applicable.

BACKGROUND OF THE INVENTION

1. Technical Field

The present invention relates to a process for preparing submicron sized nanoparticles of a poorly water soluble compound by lyophilizing a dispersion of a multiphase system having an organic phase and an aqueous phase, the organic phase having the poorly water soluble compound therein. The method is preferably used to prepare nanoparticles of a poorly water soluble, pharmaceutically active compound suitable for in vivo delivery, particularly by parenteral routes.

2. Background of the Invention

There are an ever increasing number of pharmaceutical drugs being formulated that are poorly soluble or insoluble in aqueous solutions. Such drugs provide challenges to delivering them in an injectable form such as through parenteral administration. Drugs that are insoluble in water can have significant benefits when formulated as a stable suspension of submicron sized particles. Accurate control of particle size is essential for safe and efficacious use of these formulations.

Particles must be less than seven microns in diameter to safely pass through capillaries without causing emboli (Allen et al., 1987; Davis and Taube, 1978; Schroeder et al., 1978; Yokel et al., 1981). One solution to this problem is the production of extremely small particles of the insoluble drug candidate and the creation of a microparticulate or nanoparticulate suspension. In this way, drugs that were previously unable to be formulated in an aqueous based system can be made suitable for parenteral administration. Suitability for parenteral administration includes small particle size (<7 µm), low toxicity (as from toxic formulation components or residual solvents), and bioavailability of the drug particles after administration.

The parenteral administration of such poorly water soluble pharmaceutical agents has been achieved in the past using emulsions composed of a hydrophobic solvent (e.g., oil) and a stabilized drug dispersed within an aqueous medium, such as a buffer solution or normal saline solution. These liquid/liquid emulsions may be injected intravenously.

One example of this approach utilized the anesthetic, propofol (2,6 diisopropylphenol), in which the pharmacological agent was dissolved within a vegetable oil emulsion to enable intravenous administration. See, e.g., U.S. Pat. Nos. 4,056,635; 4,452,817 and 4,798,846, all to Glen et al. Such emulsions, however, tend to be unstable given the predominance of the oil phase and the absence of antimicrobial agents. In other instances, even where the pharmacological agent is successfully incorporated into an oil-free formulation, particles containing the pharmacological agent may cause irritation at the site of delivery because of their size or form. Furthermore, many insoluble drugs of interest do not show appreciable solubility within traditional oil emulsion systems. One reason for this is that solubility is not strictly defined by polarity, but also includes hydrogen bonding, dipole-dipole interactions, ionic stabilization and atom to atom interactions.

U.S. Pat. No. 4,073,943, issued to Wretlind et al., discloses a method of administering a water-insoluble pharmaceutically active agent by dissolving the agent in oil and emulsifying the solution with water in the presence of surfactants (egg phosphatides, pluronics, polyglycerol oleate, etc.) to form stable lipoid particles of the agent dispersed in the aqueous phase.

U.S. Pat. No. 4,540,602, issued to Motoyama et al., discloses a process for the preparation of an activated pharmaceutical composition containing a water insoluble drug for oral administration. In one procedure of the invention (see Examples 4 to 10), the process is carried out by dissolving the drug in hydrophobic organic solvents, and the resulting solution is emulsified in water. The dispersing medium is then removed rapidly by spray drying, resulting in particles ranging in particle size of from about 0.1 to about 3.0 µm.

A variety of approaches have been explored for developing stable formulations of a substantially water-insoluble pharmacologically active agent for in vivo delivery. One approach is directed to the production of suspended particles coated with protein. U.S. Pat. No. 5,916,596, issued to Desai et al., discloses the application of high shear to a mixture of an organic phase having a pharmacologically active agent dispersed therein and an aqueous medium containing a biocompatible polymer. The mixture is sheared in a high pressure homogenizer at a pressure in the range of from about 3,000 to 30,000 psi. The '596 patent provides that the mixture must contain substantially no surfactants because the combined use of a surfactant with a protein results in the formation of large, needle-like crystalline particles that increase in size during storage. See columns 17-18, example 4. The biocompatible polymer may be crosslinked as the result of exposure to the high shear conditions in a high pressure homogenizer. In the embodiment in which protein containing sulfhydryl or disulfide groups is used (e.g. albumin), the protein forms a crosslinked shell around droplets of non-aqueous medium. See Column 8, lines 35-48. In Examples 1, 2, 5, 6, 9, 10, 11, and 12, the organic phase is removed rapidly by rotary evaporation at 40° C. and at a reduced pressure of 30 mm Hg, resulting in an aqueous dispersion of particles coated with crosslinked protein. The aqueous dispersion may further be lyophilized to remove the aqueous phase. The '596 patent discloses other alternative methods of removing the solvent, including falling film evaporation, spray drying, and freeze-drying. Example 2 discloses that the crude emulsion may be sonicated to produce nanoparticles ranging from 350-420 nanometers. Example 5 discloses a method to prepare sterile-filterable nanoparticles of less than 200 nm. This method requires that the pharmaceutical agent is initially dissolved in a mixture of substantially water immiscible organic solvent (e.g., chloroform) and a water miscible organic solvent (e.g. ethanol).

U.S. Pat. No. 5,560,933, issued to Soon-Shiong et al., discloses the formation of a polymeric shell around the water-insoluble oil (containing the drug) for in vivo delivery. The method discloses the application of sonication to a mixture comprising a polymer-containing aqueous medium and a dispersing agent (oil) having a substantially water-insoluble drug dispersed therein. In this reference, sonication is used to drive the formation of disulfide bonds in the polymer, causing it to crosslink so as to produce a polymeric shell around the drug. Sonication is conducted for a time sufficient for the disulfide bonds to form.

In U.S. Pat. No. 5,665,383, Grinstaff et al. discloses the application of ultrasound to a single-phase, i.e., an aqueous medium, to encapsulate an immunostimulating agent within a polymeric shell for in vivo delivery. The ultrasound promotes crosslinking of the encapsulating agent by disulfide bonds to form the shell.

Another approach to preparing a water-insoluble drug for in vivo delivery centers on reducing the size of the particles that deliver the drug. In one such series of patents, which include U.S. Pat. Nos. 6,228,399; 6,086,376; 5,922,355; and 5,660,858, Parikh et al. discloses that sonication may be used to prepare microparticles of the water-insoluble compound. Of these patents, U.S. Pat. No. 5,922,355 discloses an improvement to a method that uses sonication for making the smaller particles. The improvement comprises mixing an active pharmacological agent with a phospholipid and surfactants in a single-phase aqueous system and applying energy to the system to produce the smaller particles.

U.S. Pat. No. 5,091,188, issued to Haynes, also discloses reducing the size of particles of a pharmacologically active water-insoluble drug and employing a lipid coating on the particles to confer a solid form. The patent is directed to a pharmaceutical composition of an aqueous suspension of solid particles of the drug having a diameter of about 0.05 to about 10 microns. The lipid coating affixed to the surface of the particles contributes to their solid form. The composition is produced by adding the drug to water and then reducing the particle size within the aqueous suspension. Example 6 of this reference discloses the use of a pharmacologically acceptable oil, which is selected for its inability to dissolve the crystalline drug. See column 16, lines 8-12.

Still another approach for preparing microparticles of a pharmacological agent focuses on the use of phase inversion principles. U.S. Pat. Nos. 6,235,224 B1 and 6,143,211, both issued to Mathiowitz et al., disclose the use of phase inversion phenomena to precipitate microencapsulated microparticles. The method includes mixing a polymer and a drug with a solvent. This mixture is introduced into an effective amount of a miscible nonsolvent, thereby causing spontaneous formation of the microencapsulated product.

Microprecipitation by pH shifting is another technology used to prepare dispersions of a nanoparticulate pharmaceutical agent. See, e.g., U.S. Pat. Nos. 5,665,331; and 5,662,883. This technology involves dissolving a pharmaceutical in an aqueous base that is then neutralized to form a dispersion.

In yet another approach, such as that disclosed in U.S. Pat. No. 5,766,635, issued to Spenlenhauer et al., nanoparticles have been prepared by dissolving a poly(ethylene) oxide and/or poly(propylene) oxide in an organic solvent, mixing the organic solution so formed with an aqueous solution to cause nanoparticles to precipitate out of solution, and microfluidizing the precipitated solution without the use of surfactants.

The commonly assigned and co-pending U.S. application Ser. Nos. 09/874,499; 09/874,799; 09/874,637; 09/953,979; and 10/021,692, which are incorporated herein by reference and made a part hereof, disclose a process for preparing submicron particles by microprecipitation. The process disclosed includes the steps of: (1) dissolving an organic compound in a water miscible first organic solvent to create a first solution; (2) mixing the first solution with a second solvent of water to precipitate the organic compound to create a presuspension; and (3) adding energy to the presuspension in the form of high-shear mixing or heat to provide a stable form of the organic compound having the desired size ranges. One or more optional surface modifiers can be added to the first organic solvent or the second aqueous solution.

The commonly assigned and co-pending U.S. application Ser. No. 09/964,273, which is incorporated herein by reference and made a part hereof, discloses a process for preparing submicron particles by sonicating a crude emulsion of a multiphase phase system having an organic phase and an aqueous phase, the organic phase having a pharmaceutically active compound therein. The organic phase is evaporated from the emulsion under specific sonication conditions in order to generate the drug particles. The particle formed by this process typically has an average effective particle size of less than 2 μm.

Because of the difficulties posed by poorly soluble drugs in drug therapy, the need for new technologies continues to expand for addressing these problems.

SUMMARY OF THE INVENTION

The present invention relates to a process for preparing submicron sized particles of a poorly water soluble compound. Preferably, the compound is a pharmaceutically active compound. The process comprises the steps of: (1) providing a crude dispersion of a multiphase system having an organic phase and an aqueous phase, the organic phase having a pharmaceutically active compound therein; (2) providing energy to the crude dispersion to form a microdroplet or fine dispersion; (3) freezing the fine dispersion; and (4) lyophilizing the frozen dispersion to obtain particles having a mean particle size of less than 500 nm. In a preferred embodiment, the particles have a mean particle size of less than 200 nm. In an embodiment, the organic phase is water immiscible. In another embodiment, the organic phase is partially water miscible. In yet another embodiment, the organic phase includes a co-solvent for the pharmaceutically active compound. The method for providing the crude dispersion of the multiphase system may include shaking, agitating, vortexing, and mixing. The method for providing energy to the crude dispersion to form the fine dispersion may include sonication, homogenization, high speed mixing, mechanical agitation, extrusion, microfluidization or any energy addition method sufficient to provide dispersed droplets less than 2 microns. In one embodiment, the dispersion includes solid particles in one or more phases in the multiphase system. In a preferred embodiment, the multiphase system contains one or more surface active compounds and/or other excipients. A preferred surface active compound is albumin. The particles obtained in the present invention are preferably amorphous. For pharmaceutical applications, the fine droplet dispersion can be sterile filtered before freezing and lyophilizing, and the lyophilized particles can be redispersed in an appropriate aqueous medium. This preparation is suitable for in vivo delivery by parental administration. In a preferred embodiment, the particles in the present invention are substantially free of contamination from residual organic solvent in the organic phase of the multiphase system (e.g., less than 5 ppm).

These and other aspects and attributes of the present invention will be discussed with reference to the following drawings and accompanying specification.

DETAILED DESCRIPTION OF THE PREFERRED EMBODIMENT

Figure 1:
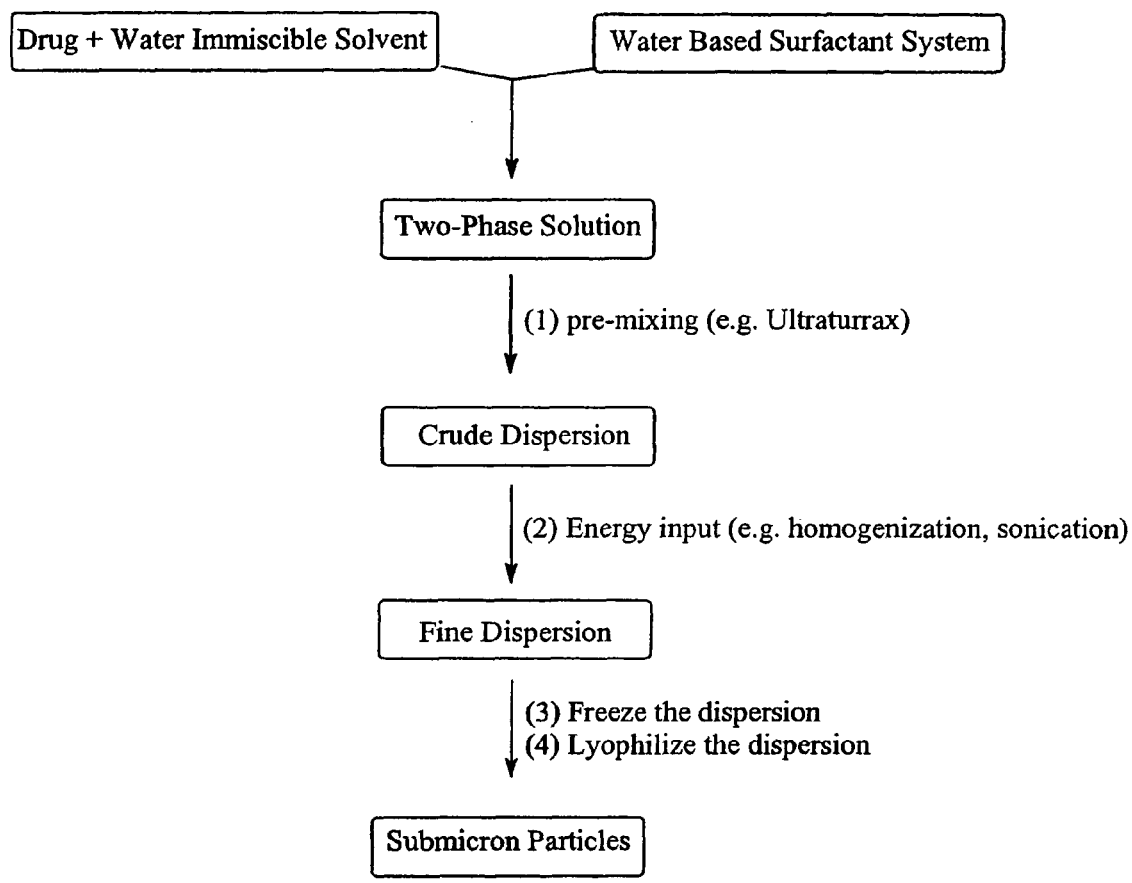
FIG. 1 is a schematic diagram of preferred steps of the present invention.

While this invention is susceptible of embodiment in many different forms, there is shown in the drawing, and will be described herein in detail, specific embodiments thereof with the understanding that the present disclosure is to be considered as an exemplification of the principles of the invention and is not intended to limit the invention to the specific embodiments illustrated.

Referring to FIG. 1, the present invention provides a process for preparing submicron-sized nanoparticles. The process includes the steps of: (1) providing a crude dispersion of a multiphase system having an organic phase and an aqueous phase, the organic phase having a pharmaceutically active compound with or without modifiers dissolved therein; (2) providing energy conditions to the crude dispersion to form a fine dispersion having an average effective oil droplet size of less than about 2 μm; (3) freezing the fine dispersion so that the bulk phase is minimally in a frozen state; and (4) lyophilizing the dispersion to obtain nanoparticles having a mean particle size of less than 500 nm, and preferably less than 200 nm.

The preferred step of providing the crude dispersion of the multiphase system includes the steps of: (1) mixing a water immiscible solvent with the pharmaceutically active compound to define an organic solution, (2) preparing an aqueous based solution, and (3) mixing the organic solution with the aqueous solution to form the multiphase dispersion system. The water immiscible solvent used may be partially water miscible and the organic solution in the system may further include a co-solvent. The multiphase system may also include one or more surface active compounds which can be added to the aqueous based solution, or to the organic solution, or to the both the aqueous solution and the organic solution, or to the mixture of the aqueous solution and the organic solution. The multiphase system can be agitated or mixed to form a crude dispersion. The crude dispersion can also be formed by any other low-energy input processes known in the art, such as shaking, vortexing, agitating, mixing (e.g. Ultraturrax) or stirring. In a preferred embodiment of the invention, the crude dispersion is formed by mixing the multiphase system with an Ultraturrax-T25 mixer for 10 seconds. The crude dispersion will have oil droplets in the water of a size of approximately less than 2 μm in diameter. The crude dispersion is subjected to addition of energy to define a microdispersion or submicron oil in water suspension. Examples of methods for providing energy to the crude dispersion include sonication, homogenization, microfluidization or other appropriate high shear techniques.

What is meant by the term "multiphase system" is a dispersion having at least one organic phase and at least one aqueous phase and in a preferred form of the invention is an oil in water (O/W) emulsion where the water phase forms the continuous phase and the oil phase forms the dispersed phase. The organic phase is preferably a water immiscible or a partially water miscible organic solvent. The organic phase may also include a co-solvent for the pharmaceutically active compound. A preferred co-solvent is a water miscible organic solvent, such as ethanol, methanol, and acetone. The ratio by weights of the organic phase to the aqueous phase is from about 1:99 to about 99:1, more preferably from 1:99 to about 40:60, and most preferably from about 2:98 to about 30:70, or any range or combination of ranges therein. The present invention further contemplates utilizing reverse emulsions or water in oil emulsion (W/O) where the oil phase forms the continuous phase and water the dispersed phase. The present invention further contemplates utilizing emulsions having more than two phases such as an oil in water in oil emulsion (O/W/O) or a water in oil in water emulsion (W/O/W). The present invention is intended in forming a liquid in liquid dispersion multiphase system. Submicron sized particles are formed when the liquid phases of the multiphase system are removed by, for example, lyophilization. Furthermore, such a dispersion system can be sterile filtered. However, solid particles may be formed during the process of forming the crude dispersion or the fine dispersion. These solid particles may be dispersed in the organic phase and/or the aqueous phase of the multiphase system.

What is meant by the term "pharmaceutically active compound" is any compound that has therapeutic effect and more particularly to such compounds that are insoluble or slightly soluble in water with a solubility of preferably less than 10 mg/ml, and more preferably less than 8 mg/ml. Such compounds can be found in the Physicians' Desk Reference. Particularly suitable pharmaceutically active compounds include, but are not limited to, antihyperlipidemics; antimicrobials, e.g., antibacterials such as sulfadiazine, antifungals such as itraconazole; non-steroidal anti-inflammatory drugs, e.g., indomethacin; antihypercholesteremic agents, e.g., probucol; and steroidal compounds, e.g., dexamethasone; immunosuppresants, e.g., cyclosporin A, tacrolimus, and mycophenolate mofetil. Or the organic compound might be from the group used as adjuvants or excipients in pharmaceutical preparations and cosmetics, such as, but not limited to, preservatives, e.g., propylparaben.

The pharmaceutically active compound can be present in a concentration to the extent it is soluble in the organic phase. In a preferred form of the invention the pharmaceutically active compound can be present in an amount from less than 1% to about 40%, more preferably from about 1% to about 25%, and most preferably from about 1% to about 10% by weight of the organic phase, or any range or combination of ranges therein.

What is meant by the term "water immiscible solvent" are those solvents which form an interfacial meniscus when combined with an aqueous solution in a 1:1 ratio (o/w). In a preferred form of the invention the water immiscible solvent will have a vapor pressure higher than that of water when both the solvent and water are measured at room temperature. Suitable water immiscible solvents include, but are not limited to, substituted or unsubstituted, linear, branched or cyclic alkanes with a carbon number of 5 or higher, substituted or unsubstituted, linear, branched or cyclic alkenes with a carbon number of 5 or higher, substituted or unsubstituted, linear, branched or cyclic alkynes with a carbon number of 5 or higher; aromatic hydrocarbons completely or partially halogenated hydrocarbons, ethers, esters, ketones, mono-, di- or tri-glycerides, native oils, alcohols, aldehydes, acids, amines, linear or cyclic silicones, hexamethyldisiloxane, or any combination of these solvents. Halogenated solvents include, but are not limited to carbon tetrachloride, methylene chloride, chloroform, tetrachloroethylene, trichloroethylene, trichloroethane, hydrofluorocarbons, chlorinated benzene (mono, di, tri), trichlorofluoromethane. Particularly suitable solvents are methylene chloride, chloroform, diethyl ether, toluene, xylene and ethyl acetate. What is meant by "partially water miscible solvents" are those solvents which are water immiscible at one concentration, and water miscible at another lower concentration. These solvents are of limited water miscibility and capable of spontaneous emulsion formation. Examples of partially water miscible solvents are tetrahydrofuran (THF), propylene carbonate, benzyl alcohol, and ethyl acetate.

What is meant by the term "fine dispersion" is a system where one liquid is dispersed into a second liquid (bulk phase) that may or may not contain emulsifying agents and the dispersed droplets have an average droplet size less than 1 micron. Such fine dispersion systems may or may not be thermally stable. During the formation of the fine dispersion, solid particles may be formed. These solid particles may be dispersed in one or more phases in the system.

What is meant by the term "surface active compounds" are compounds such as an anionic surfactant, a cationic surfactant, a zwitterionic surfactant, a nonionic surfactant or a biological surface active molecule. The surface active compound can be added to the organic phase, the aqueous phase or to both the organic phase and the aqueous phase. The surface active compound should be present in an amount by weight of the aqueous phase or the organic phase, whatever the case may be, from less than about 1% to about 30%, more preferably from about 1% to about 20%, or any range or combination of ranges therein.

Suitable anionic surfactants include but are not limited to: potassium laurate, sodium lauryl sulfate, sodium dodecylsulfate, alkyl polyoxyethylene sulfates, sodium alginate, dioctyl sodium sulfosuccinate, phosphatidyl choline, phosphatidyl glycerol, phosphatidyl inosine, phosphatidylserine, phosphatidic acid and their salts, glyceryl esters, sodium carboxymethylcellulose, cholic acid and other bile acids (e.g., cholic acid, deoxycholic acid, glycocholic acid, taurocholic acid, glycodeoxycholic acid) and salts thereof (e.g., sodium deoxycholate, etc.).

Suitable cationic surfactants include, but are not limited to, quaternary ammonium compounds, such as benzalkonium chloride, cetyltrimethylammonium bromide, lauryldimethylbenzylammonium chloride, acyl carnitine hydrochlorides, or alkyl pyridinium halides. As anionic surfactants, phospholipids may be used. Suitable phospholipids include, for example phosphatidylcholine, phosphatidylethanolamine, phosphatidylserine, phosphatidyl inositol, phosphatidylglycerol, phosphatidic acid, lysophospholipids, egg or soybean phospholipid or a combination thereof. The phospholipid may be salted or desalted, hydrogenated or partially hydrogenated or natural, semisynthetic or synthetic.

Suitable nonionic surfactants include: polyoxyethylene fatty alcohol ethers (Macrogol and Brij), polyoxyethylene sorbitan fatty acid esters (Polysorbates), polyoxyethylene fatty acid esters (Myj), sorbitan esters (Span), glycerol monostearate, polyethylene glycols, polypropylene glycols, cetyl alcohol, cetostearyl alcohol, stearyl alcohol, aryl alkyl polyether alcohols, polyoxyethylene-polyoxypropylene copolymers (poloxomers), polaxamines, methylcellulose, hydroxycellulose, hydroxy propylcellulose, hydroxy propylmethylcellulose, noncrystalline cellulose, polysaccharides including starch and starch derivatives such as hydroxyethylstarch (HES), polyvinyl alcohol, and polyvinylpyrrolidone. In a preferred form of the invention, the nonionic surfactant is a polyoxyethylene and polyoxypropylene copolymer and preferably a block copolymer of propylene glycol and ethylene glycol. Such polymers are sold under the tradename POLOXAMER also sometimes referred to as PLURONIC®, and sold by several suppliers including Spectrum Chemical and Ruger. Among polyoxyethylene fatty acid esters is included those having short alkyl chains. One example of such a surfactant is SOLUTOL® HS 15, polyethylene-660-hydroxystearate, manufactured by BASF Aktiengesellschaft.

Surface active biological molecules include such molecules as albumin, casein, heparin, hirudin, hetastarch or other appropriate biocompatible agents.

In a preferred form of the invention, the aqueous phase includes a protein as the surface active compound. A preferred protein is albumin. The protein may also function as an excipient. In embodiments in which protein is not the surface active compound, other excipients may be included in the multiphase system. Suitable excipients include, but are not limited to, saccharides, disaccharides, and sugar alcohols. A preferred disaccharide is sucrose, and a preferred sugar alcohol is mannitol.

Formation of the Fine Dispersion

While various energy addition methods can be used to form the fine dispersion from the crude dispersion, the preferred methods are sonication and homogenization. In the methods using sonication, any suitable sonication device can be used. Examples of suitable sonication device include Branson Model S-450A or Cole-Parmer 500/750 Watt Model. Such devices are well known in the industry. Typically the sonication device has a sonication horn or probe that is inserted into the multiphase system of interest to emit sonic energy into the solution. The sonicating device, in a preferred form of the invention, is operated at a frequency of from about 1 kHz to about 90 kHz and more preferably from about 20 kHz to about 40 kHz or any range or combination of ranges therein. The probe sizes can vary and preferably is in distinct sizes such as 1 inch, ½ inch or ¼ inch or the like. It may also be desirable to cool the solution during sonication to temperatures below room temperature. In the methods using homogenization, any suitable homogenization device can be used. One example of such a device is the Avestin Emulsiflex-C5 homogenizer operating at about 5,000 psi to about 30,000 psi, and preferably from about 10,000 to 20,000 psi. In Example 4, an Avestin Emulsiflex-C5 homogenizer is used to form the fine dispersion. In this example, the crude dispersion is homogenized at 10,000 to 15,000 psi for 5 minutes in the temperature range of 23° C. to 30° C. Other suitable energy addition methods to form the fine dispersion include, but are not limited to, high speed mixing, mechanical agitation, extrusion, microfluidization and other appropriate high shear techniques sufficient to provide dispersed droplets less than 2 microns.

Exposing the crude dispersion droplets to shear energy can reduce the droplet sizes to form a fine dispersion. Addition of energy to the crude dispersion by methods such as sonication or homogenization provides a source of shear energy that effectively reduces the diameters of the dispersion droplets. Shear forces from sonication or homogenization results from the compression and rarefaction of the propagation medium of the sound waves as well as mechanical shear from components of such systems. In pure liquids this oscillation between compression and rarefaction is sufficiently energetic to cause cavitation. In a dispersion, the analogous process results in tearing the dispersed liquid particles into smaller particles.

Removing of the Liquid Phase of the Fine Dispersion

Figure 2:
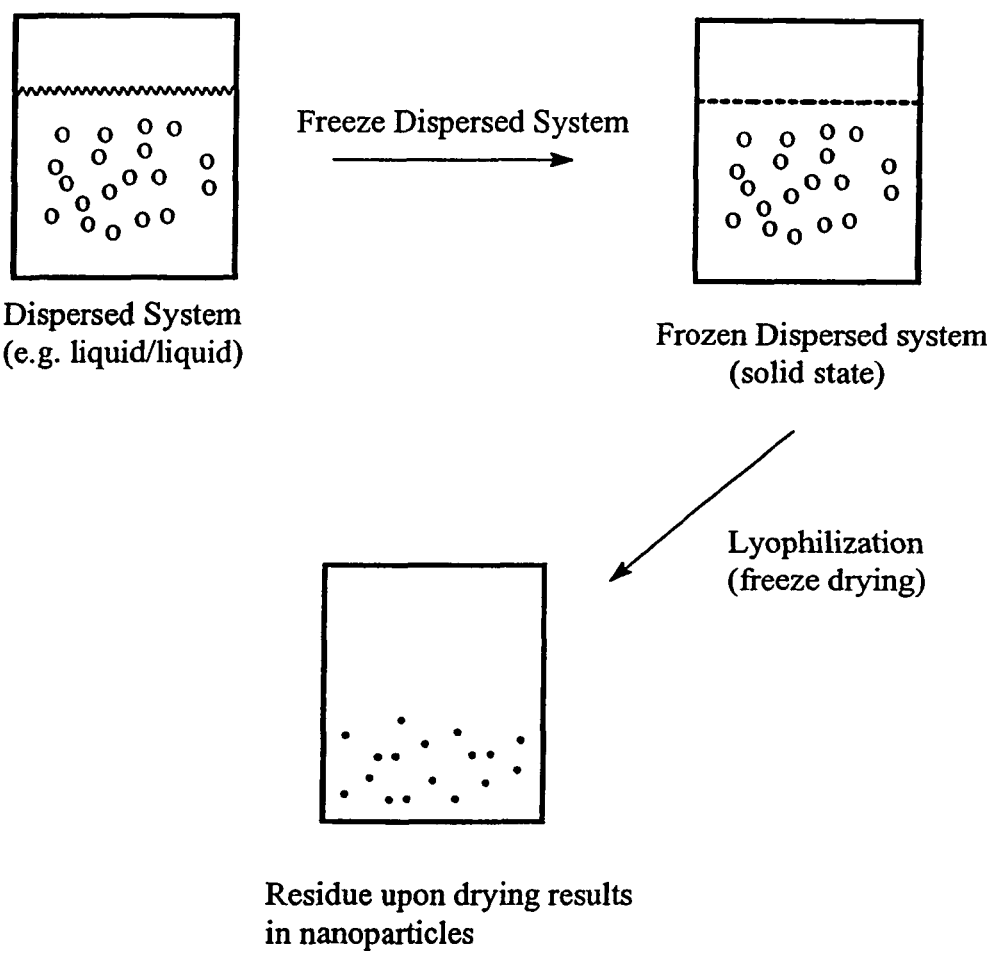
FIG. 2 is a schematic diagram of the steps of freezing and lyophilizing a dispersion to obtain submicron sized particles of the present invention.

The present invention further removes the bulk liquid phase of the fine dispersion, including the remaining water immiscible organic solvent, to obtain the submicron sized particles. The sonicated or homogenized dispersion is first frozen to form a solid bulk state, which is then followed by lyophilization (e.g., using a Vertis Sentry bench model lyophilizer). (See FIG. 2). The solid product obtained upon lyophilization results in nanoparticles having a mean particle size of less than 500 nm in diameter as determined by light scattering (HORIBA) or microscopic measurements, and preferably less than 200 nm. The dry nanoparticles prepared in the present invention are preferably substantially free of any residual organic solvent from the organic phase of the multiphase system. The term "substantially free" means that the residual organic solvent present in the dry particles is substantially less than the level of solvent regarded as acceptable from a toxicological standpoint, for example, 5 ppm or less.

The particles generally have a spherical shape. Furthermore, in a preferred form of the invention the particles will be amorphous. What is meant by amorphous is an X-ray crystal study of the particles shows virtual absence of x-ray peaks.

Sterilization of the Fine Dispersion and Redispersing of the Nanoparticles

In another preferred form of the invention, the fine dispersion is sterilized before being frozen. The preferred method of sterilization is sterile filtration using a 0.22 µm membrane filter. The nanoparticles obtained from lyophilization may further be redispersed in an appropriate aqueous dispersing medium, such as water, normal saline, buffered solutions, buffered saline, and the like. The redispersed nanoparticle suspension is now suitable for in vivo delivery by parenteral administration. Modes of parenteral administration include intravenous, intra-arterial, intrathecal, intraperitoneal, intraocular, intra-articular, intramuscular, subcutaneous injection, and the like. The preferred mode of parenteral administration is intravenous.

EXAMPLE 1

Nanoparticles of Itraconazole Using Sonication to Create the Fine Dispersion

Itraconazole (0.5 grams) was dissolved in 3 mL of methylene chloride and combined with 50 mL of a 5% albumin solution. The combined solutions were manually shaken to effect dispersion of the two liquids. The crude dispersion was than sonicated at 5° C. for 6 minutes (sonicating every other 30 seconds using a ¼" probe at 20% amplitude). The sonicated solution was frozen at −80° C. and subsequently lyophilized. The lyophilized product was analyzed by light scattering detection (HORIBA), which revealed particles having a mean diameter of 187 nm.

EXAMPLE 2

Nanoparticles of Cyclosporin Using Sonication to Create the Fine Dispersion

The general process described in example 1 was repeated except cyclosporin was used in place of itraconzole. Final particle size was 185 nm (HORIBA light scattering analysis).

EXAMPLE 3

Dispersion Lyophilization (Using Homogenization as the Energy Addition Step)

Itraconazole (0.5 grams) was dissolved in 5.0 mL of dichloromethane and mixed with 50 mL of a 5% albumin solution. This was made into a crude dispersion by treatment with an Ultraturrax-T25 mixer for 10 seconds. The crude dispersion was homogenized at 10,000-12,000 psi using an Avestin Emulsiflex C5 homogenizer for 6 passes in the temperature range of 18° C. to 27° C. to form a fine dispersion. The fine dispersion was immediately frozen at −80° C. and lyophilized without temperature control to produce a fluffy powder. The powder was reconstituted with water and the solid particle dispersion analyzed by light scattering detection (HORIBA) which revealed itraconazole particles having a mean diameter of 122 nm.

EXAMPLE 4

Sterile Filtration Incorporated into the Dispersion/lyophilization Process

Itraconazole (0.5 grams) was dissolved in 5 mL of dichloromethane and combined with 50 mL of a 5% albumin solution. The contents were then made into a crude dispersion by treatment with an Ultraturrax-T25 mixer for 10 seconds. Homogenization of the crude dispersion at 10,000 to 15,000 psi (Avestin Emulsiflex C5 homogenizer) for 5 minutes in the temperature range of 23° C. to 30° C. resulted in a microdroplet or fine dispersion. This microdroplet dispersion was easily filtered through a 0.22 µm membrane filter. Inspection of the filter did not reveal the presence of any drug material. The filtered dispersion was then frozen at −80° C. After several hours the frozen dispersion system was lyophilized without temperature control to produce a fluffy powder. The resulting lyophilized cake, containing solid itraconazole particles, was reconstituted with water and the dispersion analyzed by light scattering detection (HORIBA) to reveal itraconazole particles with a mean diameter of 144 nm.

EXAMPLE 5

Incorporation of Sodium Deoxycholate into the Process 50 mL of 5% albumin solution, 2 mL of a 2.75% sodium deoxycholate solution and 3.5 mL of a solution of itraconazole in dichloromethane containing 0.5 grams of itraconazole were mixed in a 100 mL beaker and treated with an Ultraturrax-T25 mixer for 10 seconds at 11,000 rpm. The crude dispersion was homogenized at 15,000 to 20,000 psi at room temperature to form a fine dispersion. The fine dispersion was transferred to a 250 mL glass bottle and frozen immediately at −80° C. The frozen sample was lyophilized to produce submicron particles. The lyophilized product was reconstituted with water and analyzed by light scattering detection (HORIBA), which revealed particles having a mean diameter of 207 nm.

From the foregoing, it will be observed that numerous variations and modifications may be effected without departing from the spirit and scope of the invention. It is to be understood that no limitation with respect to the specific apparatus illustrated herein is intended or should be inferred. It is, of course, intended to cover by the appended claims all such modifications as fall within the scope of the claims.

What is claimed is:
1. A process for preparing a frozen dispersed system of particles in a solid state comprising the steps of:
providing a crude dispersion of a multiphase system having an organic phase and an aqueous phase, the organic phase having a pharmaceutically active compound therein;
adding at least first and second surface active compounds to the multiphase system;
providing energy to the crude dispersion to form a fine dispersion; and freezing the fine dispersion to obtain a frozen dispersed system of particles in a solid state, the frozen dispersed system comprising the organic phase, the aqueous phase, and the particles, the particles having a mean particle size of less than 500 nm, wherein the first surface active compound is selected from the group consisting of anionic surfactants, cationic surfactants, and nonionic surfactants, and the second surface active compound comprises a surface active biological molecule.

2. The process of claim 1 wherein the particles have a mean particle size of less than 200 nm.

3. The process of claim 1 wherein the crude dispersion or the fine dispersion includes solid particles in one or more phases in the multiphase system.

4. The process of claim 1 wherein the water solubility of the pharmaceutically active compound is less than 10 mg/ml.

5. The process of claim 1 wherein the water solubility of the pharmaceutically active compound is less than 8 mg/ml.

6. The process of claim 1 wherein the multiphase system is an oil in water (O/W) emulsion.

7. The process of claim 1 wherein the multiphase system is a water in oil (W/O) emulsion.

8. The process of claim 1 wherein the multiphase system is a water in oil in water (W/O/W) emulsion.

9. The process of claim 1 wherein the multiphase system is an oil in water in oil (O/W/O) emulsion.

10. The process of claim 1 wherein the ratio by weights of the organic phase to the aqueous phase is from about 1:99 to about 99:1.

11. The process of claim 1 wherein the ratio by weights of the organic phase to the aqueous phase is from about 1:99 to about 40:60.

12. The process of claim 1 wherein the ratio by weights of the organic phase to the aqueous phase is from about 2:98 to about 30:70.

13. The process of claim 1 wherein the compound is present in an amount by weight of the organic phase from less than about 1% to about 40%.

14. The process of claim 1 wherein the compound is present in an amount by weight of the organic phase from less than about 1% to about 25%.

15. The process of claim 1 wherein the compound is present in an amount by weight of the organic phase from less than about 1% to about 10%.

16. The process of claim 1 wherein the method of providing the crude dispersion is selected from the group consisting of: shaking, agitating, vortexing, mixing, and stirring.

17. The process of claim 1 wherein the step of providing energy to the crude dispersion comprises the steps of: providing a sonication device having a transducer for emitting sonic energy; and exposing the system to said sonic energy sufficient to allow for cavitation to occur.

18. The process of claim 17 wherein the sonication device is operating at a frequency of from about 1 kHz to about 90 kHz.

19. The process of claim 17 wherein the sonication device is operating at a frequency of from about 20 kHz to about 40 kHz.

20. The process of claim 1 wherein the step of providing energy to the crude dispersion is by homogenization.

21. The process of claim 20 wherein the crude dispersion is homogenized at about 5,000 to 30,000 psi.

22. The process of claim 20 wherein the crude dispersion is homogenized at about 10,000 to 15,000 psi.

23. The process of claim 20 wherein the crude dispersion is homogenized at about 15,000 to 20,000 psi.

24. The process of claim 1 wherein at least one surface active compound is added to the organic phase.

25. The process of claim 1 wherein at least one surface active compound is added to the aqueous phase.

26. The process of claim 1 wherein at least one surface active compound is added to both the organic phase and the aqueous phase.

27. The process of claim 1 wherein the nonionic surfactant is selected from the group consisting of: polyoxyethylene fatty alcohol ethers, polyoxyethylene sorbitan fatty acid esters, polyoxyethylene fatty acid esters, sorbitan esters, glycerol monostearate, polyethylene glycols, polypropylene glycols, cetyl alcohol, cetostearyl alcohol, stearyl alcohol, aryl alkyl polyether alcohols, poloxamers, polaxamines, methylcellulose, hydroxycellulose, hydroxy propylcellulose, hydroxy propylmethylcellulose, noncrystalline cellulose, polysaccharides, polyvinyl alcohol, and polyvinylpyrrolidone.

28. The process of claim 1 wherein the anionic surfactant is selected from the group consisting of: potassium laurate, triethanolamine stearate, sodium lauryl sulfate, sodium dodecylsulfate, alkyl polyoxyethylene sulfates, sodium alginate, dioctyl sodium sulfosuccinate, phosphatidyl glycerol, phosphatidyl inositol, phosphatidylserine, phosphatidic acid and their salts, glyceryl esters, sodium carboxymethylcellulose, bile acids and their salts, cholic acid, deoxycholic acid, glycocholic acid, taurocholic acid, glycodeoxycholic acid, and calcium carboxymethylcellulose.

29. The process of claim 1 wherein the cationic surfactant is selected from the group consisting of quaternary ammonium compounds, benzalkonium chloride, cetyltrimethylammonium bromide, chitosans and lauryldimethylbenzylammonium chloride.

30. The process of claim 1 wherein the surface active biological molecule is albumin.

31. The process of claim 1 further comprising the step of adding an excipient to the multiphase system.

32. The process of claim 31 wherein the excipient is selected from the group consisting of proteins, saccharides, disaccharides, and sugar alcohols.

33. The process of claim 32 wherein the disaccharide is sucrose.

34. The process of claim 32 wherein the sugar alcohol is mannitol.

35. The process of claim 1 wherein the first and second surface active compounds are present in an amount by weight of the aqueous phase or the organic phase from less than about 1% to about 30%.

36. The process of claim 1 wherein the first and second surface active compounds are present in an amount by weight of the aqueous phase or the organic phase from less than about 1% to about 20%.

37. The process of claim 1 wherein the organic phase comprises a water immiscible solvent.

38. The process of claim 37 wherein the water immiscible solvent is selected from the group consisting of: linear, branched or cyclic alkanes with carbon number of 5 or higher, linear, branched or cyclic alkenes with carbon number of 5 or higher, linear, branched or cyclic alkynes with carbon number of 5 or higher; aromatic hydrocarbons, completely or partially halogenated hydrocarbons, ethers, esters, ketones, mono-, di- or tri-glycerides, native oils, alcohols, aldehydes, acids, amines, linear or cyclic silicones, hexamethyldisiloxane, or any combination of these solvents.

39. The process of claim 37 wherein the water immiscible solvent has a vapor pressure higher than water at room temperature.

40. The process of claim 1 wherein the organic phase comprises a partially water miscible solvent.

41. The process of claim 40 wherein the partially water miscible solvent is selected from the group consisting of: fluorinated solvents, tetrahydrofuran, propylene carbonate, benzyl alcohol, and ethyl acetate.

42. The process of claim 1 wherein the organic phase further includes a co-solvent.

43. The process of claim 42 wherein the co-solvent is a water miscible organic solvent.

44. The process of claim 1 wherein the compound is selected from the group consisting of: antihyperlipidemics, anesthetics, antiasthamatics, antimicrobials, antifungals, antineoplastics, non-steroidal anti-inflammatory drugs, antihypercholesteremic agents, analgesics, steroidal compounds, antipyretics, antidepressants, antiarrhthmics, antianxiety drugs, antimanics, antiarthritics, antihistamines, anti-infectives, water insoluble vitamins, antipsychotics, sedatives, antihypertensive agents, diagnostic agents, anticonvulsants and immunosuppresants.

45. The process of claim 1 further comprising the step of sterile filtering the fine dispersion prior to freezing.

46. The process of claim 1 wherein the first surface active compound is a nonionic surfactant.

47. The process of claim 1 wherein the first surface active compound is an anionic surfactant.

* * * * *